United States Patent
Mahapatra

(10) Patent No.: US 10,588,531 B2
(45) Date of Patent: Mar. 17, 2020

(54) METHODS AND SYSTEMS FOR DETERMINING PREVALENCE OF CARDIAC PHENOMENA

(71) Applicant: St. Jude Medical, Cardiology Division, Inc., St. Paul, MN (US)

(72) Inventor: Srijoy Mahapatra, Edina, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 156 days.

(21) Appl. No.: 15/893,007

(22) Filed: Feb. 9, 2018

(65) Prior Publication Data

US 2018/0228389 A1    Aug. 16, 2018

Related U.S. Application Data

(60) Provisional application No. 62/457,384, filed on Feb. 10, 2017.

(51) Int. Cl.
*A61B 5/02* (2006.01)
*A61B 5/044* (2006.01)
(Continued)

(52) U.S. Cl.
CPC .......... *A61B 5/044* (2013.01); *A61B 5/04012* (2013.01); *A61B 5/0422* (2013.01); *A61B 5/0452* (2013.01); *A61B 5/061* (2013.01); *A61B 5/4836* (2013.01); *A61B 5/6852* (2013.01); *A61B 5/6857* (2013.01);
(Continued)

(58) Field of Classification Search
CPC ..... A61B 18/14; A61B 5/6852; A61B 5/7282; A61B 5/04012; A61B 5/061; A61B 2018/00577
See application file for complete search history.

(56) References Cited

U.S. PATENT DOCUMENTS 6,233,476 B1    5/2001  Strommer
6,498,944 B1   12/2002  Ben Haim
(Continued)

FOREIGN PATENT DOCUMENTS

EP    1808124 A2    7/2007
EP    1808124 A3   11/2007

OTHER PUBLICATIONS

International Search Report and the Written Opinion of the International Searching Authority for PCT Application No. PCT/US2018/017605, dated May 28, 2018.

*Primary Examiner* — Mallika D Fairchild
(74) *Attorney, Agent, or Firm* — Armstrong Teasdale LLP

(57) ABSTRACT

Systems and methods for determining prevalence of a cardiac phenomenon based on electrophysiological (EP) data from a tissue of a body are provided. The EP data is measured by at least one sensor disposed on at least one medical device that is positionable near the tissue of the body. A system includes an electronic control unit communicatively coupled to a display device and configured to, for each of the plurality of locations, detect, at each of a plurality of discrete times occurring during a predetermined time period, whether a cardiac phenomenon occurs at the location based on the EP data, determine a prevalence of the cardiac phenomenon based on the detecting, and display information indicative of the determined prevalence of the cardiac phenomenon on the display device.

20 Claims, 8 Drawing Sheets

(51) Int. Cl.
*A61B 5/042* (2006.01)
*A61B 5/0452* (2006.01)
*A61B 5/00* (2006.01)
*A61B 34/10* (2016.01)
*A61B 5/04* (2006.01)
*A61B 5/06* (2006.01)
A61B 90/00 (2016.01)
A61B 18/00 (2006.01)
A61B 18/14 (2006.01)

(52) U.S. Cl.
CPC .......... *A61B 5/6858* (2013.01); *A61B 5/7282* (2013.01); *A61B 34/10* (2016.02); *A61B 18/14* (2013.01); *A61B 2018/00577* (2013.01); *A61B 2034/105* (2016.02); *A61B 2090/365* (2016.02)

(56) References Cited

U.S. PATENT DOCUMENTS

| | | |
|---|---|---|
| 6,690,963 B2 | 2/2004 | Ben Haim |
| 6,788,967 B2 | 9/2004 | Ben Haim |
| 7,197,354 B2 | 3/2007 | Sobe |
| 7,263,397 B2 | 8/2007 | Hauck |
| 7,386,339 B2 | 6/2008 | Strommer |
| 7,536,218 B2 | 5/2009 | Govari |
| 8,038,625 B2 | 10/2011 | Afonso |
| 9,186,081 B2 * | 11/2015 | Afonso |
| 2007/0197929 A1 * | 8/2007 | Porath .................. A61B 5/0422 600/523 |
| 2010/0094274 A1 | 4/2010 | Narayan |
| 2010/0168550 A1 | 7/2010 | Byrd |
| 2015/0065836 A1 | 3/2015 | Thakur |
| 2015/0119672 A1 | 4/2015 | Thakur |

* cited by examiner

METHODS AND SYSTEMS FOR DETERMINING PREVALENCE OF CARDIAC PHENOMENA

CROSS REFERENCE TO RELATED APPLICATIONS

This application claims priority to provisional application Ser. No. 62/457,384, filed Feb. 10, 2017 which is incorporated by reference in its entirety.

FIELD OF THE DISCLOSURE

This disclosure relates to systems and methods for detecting cardiac phenomena based on electrophysiological data. More particularly, this disclosure relates to computer-implemented systems and methods for determining prevalence of cardiac phenomena over time based on electrophysiological data.

BACKGROUND

It is known that various computer-based systems and computer-implemented methodologies can be used to generate multi-dimensional surface models of geometric structures, such as, for example, anatomic structures. More specifically, a variety of systems and methods have been used to generate multi-dimensional surface models of the heart and/or particular portions thereof.

The human heart muscle routinely experiences electrical currents traversing its many surfaces and ventricles, including the endocardial chamber. Just prior to each heart contraction, the heart muscle is said to "depolarize" and "repolarize," as electrical currents spread across the heart and throughout the body. In healthy hearts, the surfaces and ventricles of the heart will experience an orderly progression of a depolarization wave. In unhealthy hearts, such as those experiencing atrial arrhythmia, including for example, ectopic atrial tachycardia, atrial fibrillation, and atrial flutter, the progression of the depolarization wave may not be so orderly. Arrhythmias may persist as a result of scar tissue or other obstacles to rapid and uniform depolarization. These obstacles may cause depolarization waves to repeat a circuit around some part of the heart. Atrial arrhythmia can create a variety of dangerous conditions, including irregular heart rates, loss of synchronous atrioventricular contractions, and stasis of blood flow, all of which can lead to a variety of ailments and even death.

Medical devices, such as, for example, electrophysiology (EP) catheters, are used in a variety of diagnostic and/or therapeutic medical procedures to correct such heart arrhythmias. Typically in a procedure, a catheter is manipulated through a patient's vasculature to a patient's heart, for example, and carries one or more electrodes that may be used for mapping, ablation, diagnosis, and/or to perform other functions. Once at an intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to, from, and at the treatment site, which can invariably be a function of a user's skill level.

Before or during an ablation procedure, however, a user must measure and diagnose these undesirable electrical pathways and regions of arrhythmia "breakout." An electrogram, used to help identify these regions, is any record of change in electric potential over time, often obtained by placing an electrode directly on or near the surface of the heart tissue. To acquire electrograms, conventional techniques include point-by-point methods of recording changes in electrical potential. These changes in potential may then be mapped onto a corresponding model of an anatomical structure. In other words, these methods enable the creation of electrocardiographic maps by navigating one or more catheters around an area of interest and collecting electrogram and spatial localization data from one spot to the next and then mapping the collected data accordingly.

It is desirable to identify the sources of cardiac arrhythmias based on electrophysiological (EP) data, particularly for systems performing diagnostic, therapeutic, and ablative procedures on a patient. EP data may come from intrinsic rhythms such as, for example, Sinus Rhythm, Atrial Flutter, and Atrial Fibrillation. EP data may also come from manual interventions such as pacing and induced arrhythmias, for example.

In at least some known systems, many types of cardiac phenomena are detectable. However, the prevalence of those cardiac phenomena (i.e., how often those cardiac phenomena occur) is not determined. Accordingly, if data is collected twenty times for a particular location on a subject's heart, existing systems may indicate that a rotor is present, regardless of whether the rotor was detected only one of those twenty times, or eighteen of those twenty times. Thus, to aid clinicians, it would be desirable to be able to detect not only the presence, but also the prevalence, of one or more cardiac phenomena.

BRIEF SUMMARY OF THE DISCLOSURE

In one embodiment, the present disclosure is directed to a system for determining prevalence of a cardiac phenomenon based on electrophysiological (EP) data from a tissue of a body are provided. The EP data is measured at a plurality of locations by at least one sensor disposed on at least one medical device that is positionable near the tissue of the body. The system includes an electronic control unit communicatively coupled to a display device and configured to, for each of the plurality of locations, detect, at each of a plurality of discrete times occurring during a predetermined time period, whether a cardiac phenomenon occurs at the location based on the EP data, determine a prevalence of the cardiac phenomenon based on the detecting, and display information indicative of the determined prevalence of the cardiac phenomenon on the display device.

In another embodiment, the present disclosure is directed to a computer-implemented method of determining prevalence of a cardiac phenomenon based on electrophysiological (EP) data from a tissue of a body, the EP data measured at a plurality of locations by at least one sensor disposed on at least one medical device that is positionable near the tissue of the body. The method includes, for each of the plurality of locations, detecting, at each of a plurality of discrete times occurring during a predetermined time period, whether a cardiac phenomenon occurs at the location based on the EP data, determining a prevalence of the cardiac phenomenon based on the detecting, and displaying information indicative of the determined prevalence of the cardiac phenomenon.

In another embodiment, the present disclosure is directed to a processing apparatus for determining prevalence of a cardiac phenomenon based on electrophysiological (EP) data from a tissue of a body, the EP data measured at a plurality of locations by at least one sensor disposed on at least one medical device that is positionable near the tissue of the body. The processing apparatus is configured to, for each of the plurality of locations, detect, at each of a plurality of discrete times occurring during a predetermined time period, whether a cardiac phenomenon occurs at the location based on the EP data, determine a prevalence of the cardiac phenomenon based on the detecting, and cause information indicative of the determined prevalence of the cardiac phenomenon to be displayed on a display device.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The disclosure provides systems and methods for detecting and determining a prevalence of various cardiac phenomena. The embodiments described herein include detecting, at each of a plurality of discrete times occurring during a predetermined time period, whether a cardiac phenomenon occurs at a location. A prevalence of the cardiac phenomenon (i.e., how often the cardiac phenomenon occurs) is determined based on the detecting. Further, information indicative of the determined prevalence is displayed to a user (e.g., a clinician).

Figure 1:
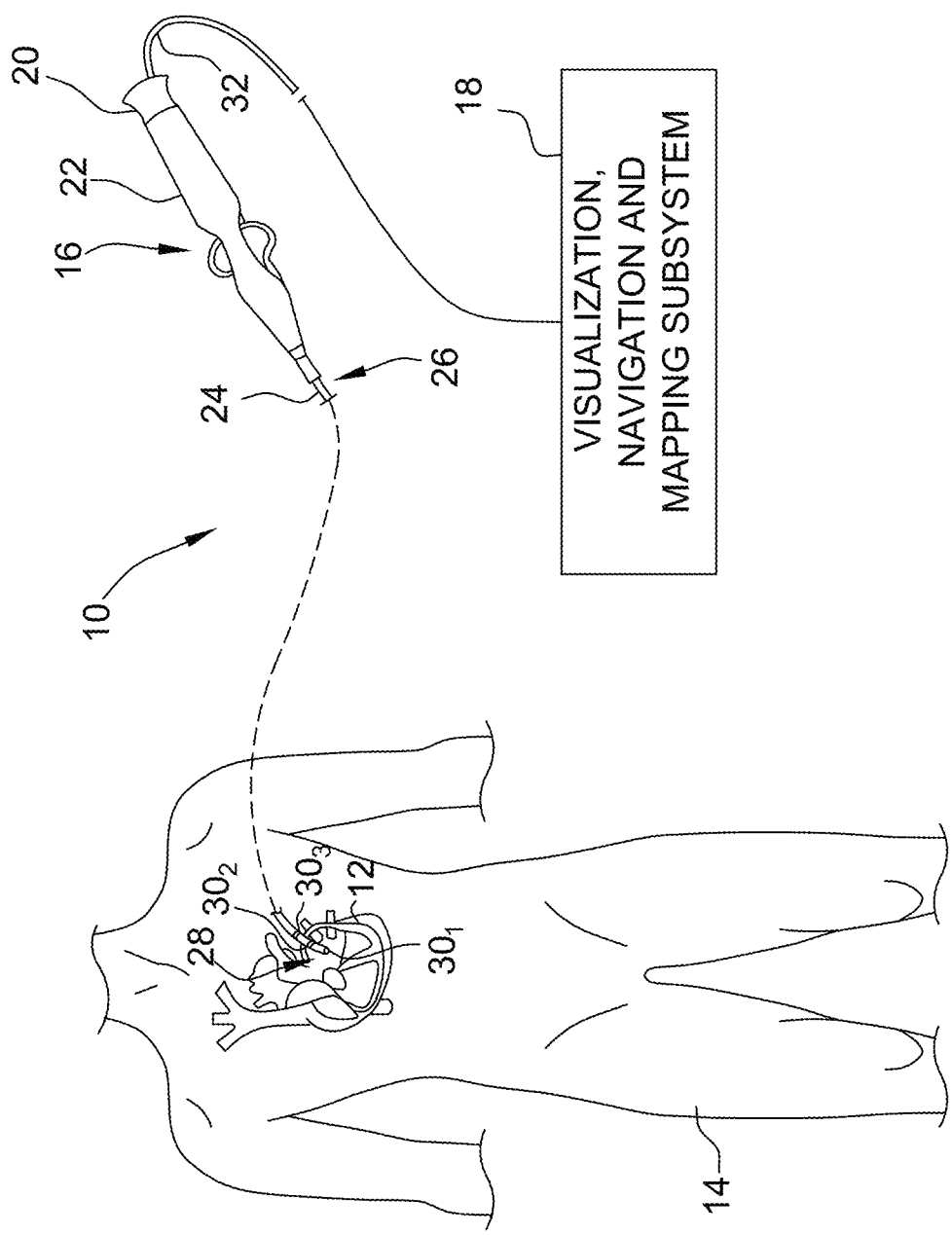
FIG. 1 is a schematic and diagrammatic view of a system for performing at least one of a diagnostic and a therapeutic medical procedure in accordance with present teachings.

Referring now to the drawings wherein like reference numerals are used to identify identical components in the various views, FIG. 1 illustrates one exemplary embodiment of a system 10 for performing one or more diagnostic and/or therapeutic functions on or for a tissue 12 of a body 14. In an exemplary embodiment, tissue 12 includes heart or cardiac tissue within a human body 14. It should be understood, however, that system 10 may find application in connection with a variety of other tissues within human and non-human bodies, and therefore, the present disclosure is not meant to be limited to the use of system 10 in connection with only cardiac tissue and/or human bodies.

System 10 may include a medical device (e.g., a catheter 16) and a subsystem 18 for the visualization, navigation, and/or mapping of internal body structures (hereinafter referred to as the "visualization, navigation, and mapping subsystem 18" or "subsystem 18").

In this embodiment, medical device includes a catheter 16, such as, for example, an electrophysiology catheter. In other exemplary embodiments, medical device may take a form other than catheter 16, such as, for example and without limitation, a sheath or catheter-introducer, or a catheter other than an electrophysiology catheter. For clarity and illustrative purposes only, the description below will be limited to embodiments of system 10 wherein medical device is a catheter (catheter 16).

Catheter 16 is provided for examination, diagnosis, and/or treatment of internal body tissues such as tissue 12. Catheter 16 may include a cable connector 20 or interface, a handle 22, a shaft 24 having a proximal end 26 and a distal end 28 (as used herein, "proximal" refers to a direction toward the end of catheter 16 near handle 22, and "distal" refers to a direction away from handle 22), and one or more sensors, such as, for example and without limitation, a plurality of electrodes 30 (i.e., $30_1, 30_2, \ldots, 30_N$), mounted in or on shaft 24 of catheter 16 at or near distal end 28 of shaft 24. The sensors may include, for example, impedance electrodes.

In this embodiment, each electrode 30 is configured to both acquire electrophysiological (EP) data corresponding to tissue 12, and to produce signals indicative of its three-dimensional (3-D) position (hereinafter referred to as "positioning data"). In another embodiment, catheter 16 may include a combination of electrodes 30 and one or more positioning sensors (e.g., electrodes other than electrodes 30 or magnetic sensors (e.g., coils)). In one such embodiment, electrodes 30 are configured to acquire EP data relating to tissue 12, while the positioning sensor(s) is configured to generate positioning data indicative of the 3-D position thereof, which may be used to determine the 3-D position of each electrode 30. In other embodiments, catheter 16 may further include other conventional components such as, for example and without limitation, steering wires and actuators, irrigation lumens and ports, pressure sensors, contact sensors, temperature sensors, additional electrodes and corresponding conductors or leads, and/or ablation elements (e.g., ablation electrodes, high intensity focused ultrasound ablation elements, and the like).

Connector 20 provides mechanical and electrical connection(s) for one or more cables 32 extending, for example, from visualization, navigation, and mapping subsystem 18 to one or more electrodes 30 or the positioning sensor(s) mounted on catheter 16. In other embodiments, connector 20 may also provide mechanical, electrical, and/or fluid connections for cables extending from other components in system 10, such as, for example, an ablation system and a fluid source (when catheter 16 includes an irrigated catheter). Connector 20 is disposed at proximal end 26 of catheter 16.

Handle 22 provides a location for a user to hold catheter 16 and may further provide means for steering or guiding shaft 24 within body 14. For example, handle 22 may include means to manipulate one or more steering wires extending through catheter 16 to distal end 28 of shaft 24 to steer shaft 24. It will be appreciated by those of skill in the art that the construction of handle 22 may vary. In other embodiments, the control of catheter 16 may be automated such as by being robotically driven or controlled, or driven and controlled by a magnetic-based guidance system. Accordingly, catheters controlled either manually or automatically are both within the spirit and scope of the present disclosure.

Shaft 24 is an elongate, tubular, and flexible member configured for movement within body 14. Shaft 24 supports, for example and without limitation, electrodes 30, other electrodes or positioning sensors mounted thereon, associated conductors, and possibly additional electronics used for signal processing or conditioning. Shaft 24 may also permit transport, delivery and/or removal of fluids (including irrigation fluids, cryoablation fluids, and body fluids), medicines, and/or surgical tools or instruments. Shaft 24, which may be made from conventional materials such as polyurethane, defines one or more lumens configured to house and/or transport electrical conductors, fluids, or surgical tools. Shaft 24 may be introduced into a blood vessel or other structure within body 14 through a conventional introducer. Shaft 24 may then be steered or guided through body 14 to a desired location such as tissue 12.

Distal end 28 of shaft 24 may be the main portion of catheter 16 that contains electrodes 30 or other sensors for acquiring EP data and positioning data. As described above, in one embodiment, electrodes 30 may be configured to acquire both EP data and positioning data. In another embodiment, and as will be described in greater detail below, electrodes 30 may be configured to acquire EP data while one or more positioning sensors may be configured to acquire positioning data, which may then be used to determine the respective positions of electrodes 30. Regardless of whether the positioning data is acquired by electrodes 30 or by positioning sensors, distal end 28 may be arranged in a number of configurations that facilitate the efficient acquisition, measurement, collection, or the like of EP data from tissue 12.

Figure 2:
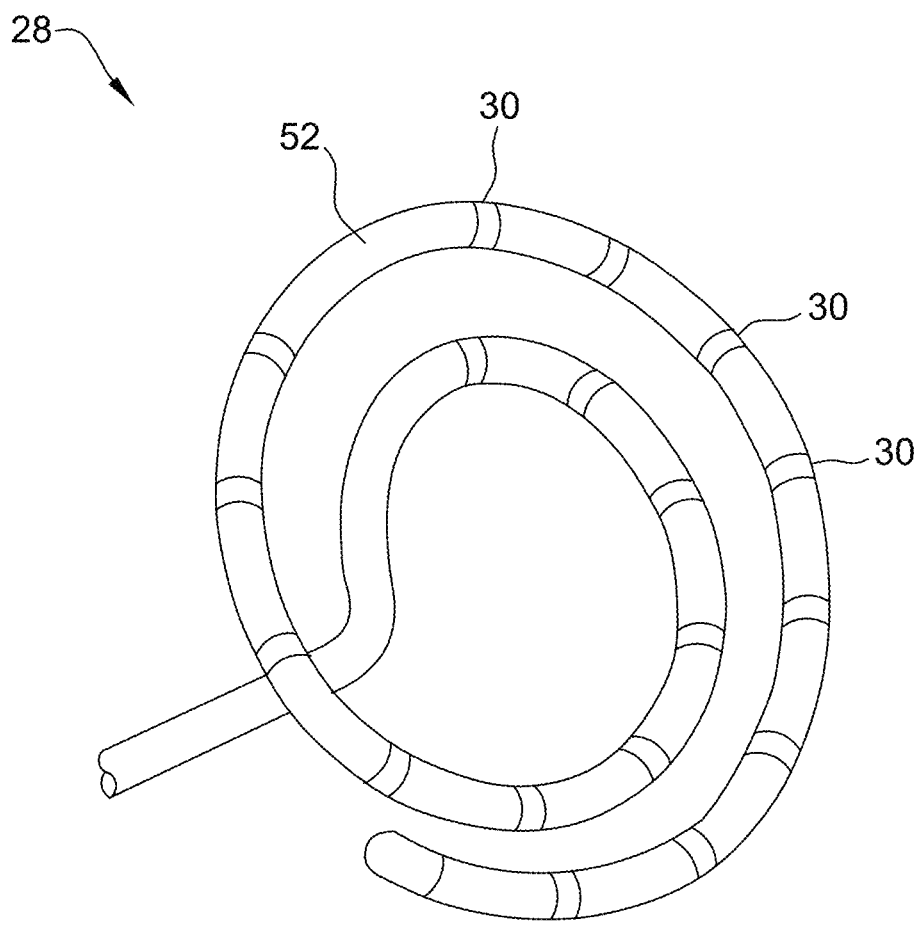
FIG. 2 is an isometric view of a distal end of one embodiment of a medical device arranged in a spiral configuration.

In one embodiment, as shown in FIG. 2, distal end 28 may be arranged in a spiral configuration. In this embodiment, the spiral configuration may be generally planar and may contain a high density of electrodes 30 for taking unipolar or bipolar measurements of EP data from tissue 12. Unipolar measurements may generally represent the electrical voltage perceived at each electrode. Bipolar measurements, though, may generally represent the electrical potential between any pair of electrodes. And as one skilled in the art will recognize, bipolar measurements may be computed from unipolar measurements. Moreover, electrodes 30 may be disposed in or along distal end 28 in a known spatial configuration such that the distances between electrodes 30 are known. The diameters of the loops, such as loop 52, may vary from one embodiment to another. In one embodiment, the diameter of the outermost loop is twenty millimeters. In an alternative embodiment, the spiral configuration may contain multiple spiral loops.

There are many advantages to placing a high density of electrodes 30 on the spiral configuration or at distal end 28 of catheter 16. Because the distribution of electrodes 30 is dense, and because of the multitude of possible unipolar and bipolar comparisons of electrodes 30, the spiral configuration may be ideal for creating high definition (HD) surface maps representative of electrical activity on tissue 12.

Figure 3:
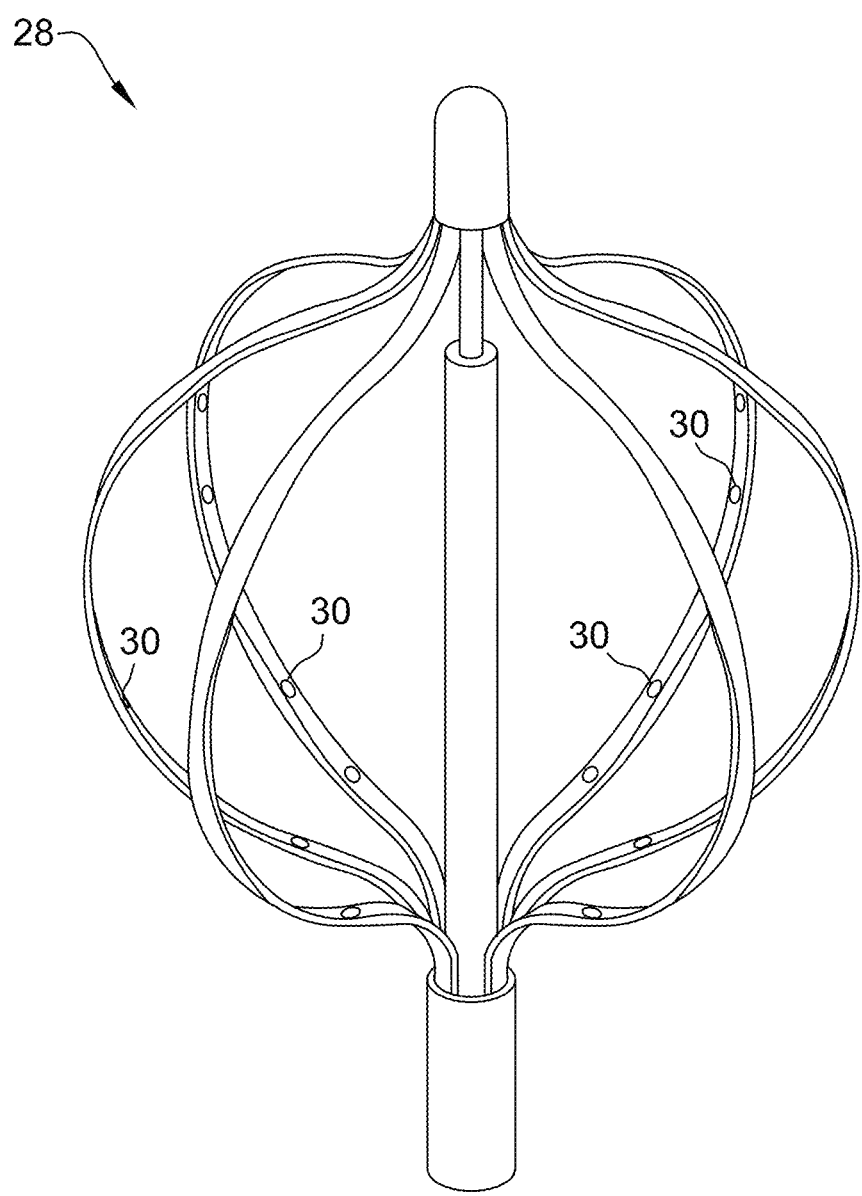
FIG. 3 is an isometric view of a distal end of another embodiment of a medical device arranged in a basket configuration.

In another embodiment, as shown in FIG. 3, distal end 28 may be arranged in a basket configuration. The basket configuration, or a similar configuration with a generally cylindrical array of electrodes 30, may contain a high density of electrodes 30. In one embodiment, electrodes 30 may be non-contact electrodes that generally need not be in contact with tissue 12 to measure EP data. In another embodiment, electrodes 30 may include both contact and non-contact electrodes.

Such non-contact electrodes may be used for unipolar analyses. It may be advantageous to analyze unipolar EP data since a unipolar electrogram morphology may provide more information regarding colliding wavefronts (presence of "R" waves in the QRS Complex known in the art), short radius reentry wavefronts (presence of the sinusoid waveform), and source wavefronts (a "QS" morphology on the electrogram at the onset of depolarization). In general, a depolarization wavefront is a group of electrical vectors that traverse tissue 12 of body 14. Depolarization wavefronts may vary in pattern, size, amplitude, speed, and the like. And some depolarization wavefronts may be relatively orderly while others may be relatively, or even entirely, disorderly.

In another embodiment, however, bipolar EP data may provide better spatial localization data, better depolarization wave directionality indications, and better alternating current (AC) electrical noise rejection. With bipolar EP data, a pair of electrodes 30 (commonly referred to as "poles" or "bi-poles") may be spaced apart, but positioned relatively close together with respect to electric fields caused by other remote parts of body 14. Thus, effects from remote electric fields may be negated since electrodes 30 are positioned close to one another and experience similar effects from the distant electric field.

Figure 4A:
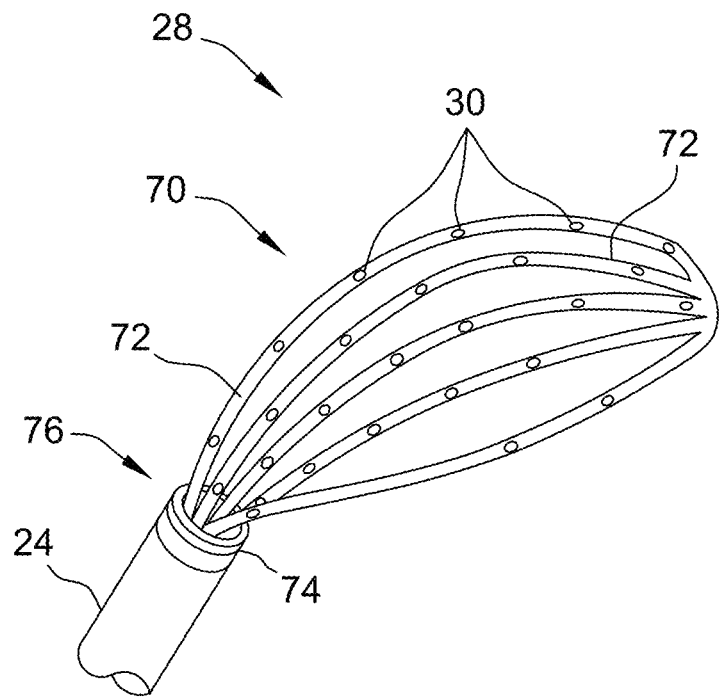
FIGS. 4A and 4B are isometric and side views, respectively, of a distal end of one embodiment of a medical device arranged in a matrix-like configuration.
Figure 4B:
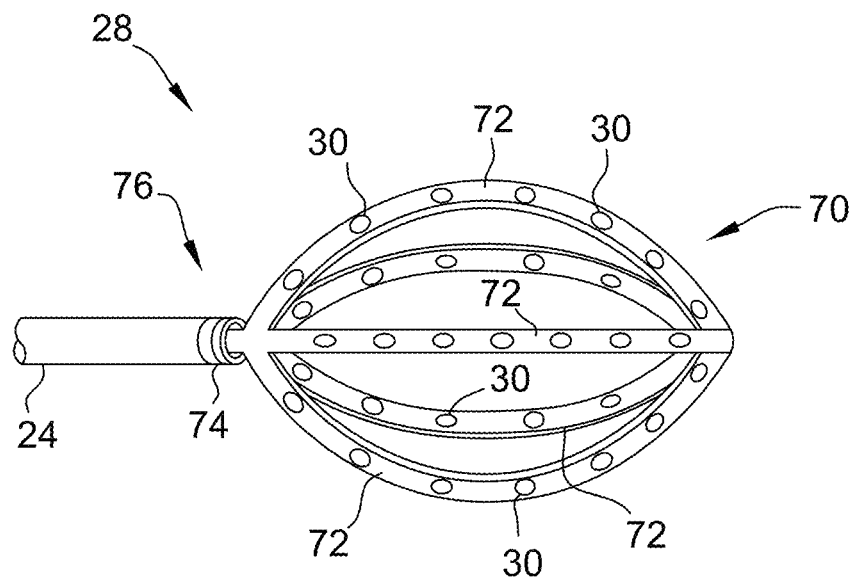

In yet another embodiment of the distal end 28 shown in FIGS. 4A and 4B, a matrix-like configuration may also be provided with a high density of electrodes 30. FIG. 4A shows an isometric view of the matrix-like configuration, while FIG. 4B shows a side view. The matrix-like configuration may have a number of splines 72 arranged side by side, with each spline 72 having at least one electrode 30 mounted thereon. Longer splines may contain more electrodes 30 to maintain a consistent electrode density throughout the matrix-like configuration.

In the embodiment shown in FIGS. 4A and 4B, the matrix-like configuration may be cupped, almost as if to have a slight scoop as seen in FIG. 4A. In another embodiment (not shown), the matrix-like configuration may be substantially flat or planar, without any scoop-like feature. While both embodiments may facilitate data measurements from tissue 12, the matrix-like configuration shown in FIG. 4A in particular may be used to acquire at least some non-contact measurements. Another possible use of the matrix-like configuration would be to help diagnose arrhythmias and direct epicardial ablation therapies in the pericardial space.

In one embodiment, the matrix-like configuration along with other configurations of distal end 28 may collapse to a streamlined profile for insertion, manipulation, and removal from body 14. In addition, or in the alternative, distal end 28 may be at least partially concealed and transported within shaft 24 when not collecting data or performing a procedure. Shaft 24 may be more streamlined than distal end 28, and therefore may provide a better vehicle for transporting distal end 28 to and from tissue 12. Once at the intended site, distal end 28 may be deployed from shaft 24 to perform the intended procedures. Likewise, after the procedures are performed, distal end 28 may be re-concealed, at least in part, within shaft 24 for removal from body 14.

One exemplary way in which the matrix-like configuration is collapsible into a streamlined profile or fully or partially deployable is to allow outer splines 72 to translate modestly within shaft 24 while anchoring innermost splines 72 to shaft 24 at a point 74 at distal end 28 thereof. Moreover, for enhanced functionality, a joint 76 may be incorporated near point 74, either for providing flexibility or for selectively deflecting distal end 28, thereby allowing distal end 28 better access to tissue 12.

Figure 5:
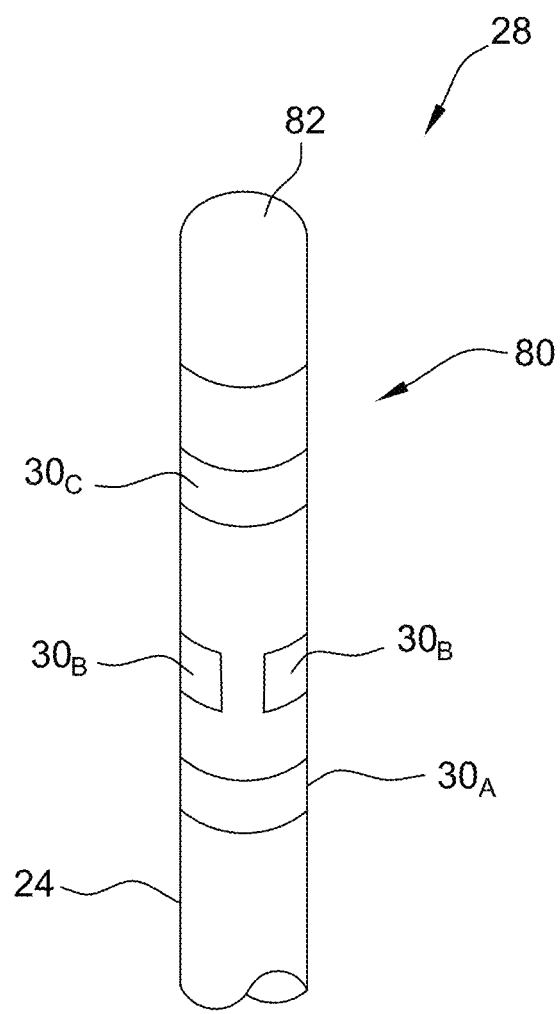
FIG. 5 is a top view of a distal end of one embodiment of a medical device wherein the medical device is a radio frequency (RF) ablation catheter.

Another exemplary embodiment of a high-density electrode catheter is illustrated in FIG. 5. In this embodiment, distal end 28 includes an ablation tip 80, and may be well suited for enhancing radio frequency (RF) ablation procedures. More particularly, the arrangement may allow for the provision of rapid positioning feedback and may also enable updates to be made to HD surface maps as the ablative procedures are being performed.

With continued reference to FIG. 5, in an exemplary embodiment wherein visualization, navigation, and mapping subsystem 18 is an electric field-based system, distal end 28 may include a proximal ring electrode $30_A$ positioned close to, yet spaced apart from, a series of spot or button electrodes $30_B$. Proximal ring electrode $30_A$ and spot electrodes $30_B$ may be used to acquire both EP data and positioning data. Spaced further distally from the spot electrodes $30_B$, a distal ring electrode $30_C$ may be disposed in or on shaft 24 so that bipolar measurements of EP data may be made between the spot electrodes $30_B$ and the distal ring electrode $30_C$. Finally, distal end 28 further includes an ablation electrode 82 for performing ablation therapies, such as, for example and without limitation, RF ablation therapies.

Visualization, navigation, and mapping subsystem 18 may determine the positions of proximal ring electrode $30_A$ (or a geometric center thereof), the spot electrodes $30_B$, and distal ring electrode $30_C$ (or a geometric center thereof) in the same manner as the position(s) of the electrode(s) 30 shown in FIG. 6, as will be described in greater detail below. Based on these positions and/or the known configuration of distal end 28 (e.g., the spacing of the various electrodes), the position of ablation electrode 82 may also be determined and, in certain embodiments, projected onto a geometrical anatomical model.

By incorporating at least three non-co-linear electrodes as is illustrated, for example, in FIG. 5, rotational information about distal end 28 (referred to as "orientation") may be calculated. Hence six degrees of freedom (three for position and three for orientation) may be determined for ablation tip 80 of catheter 16. Knowing the position and orientation of distal end 28 allows for a much simpler registration of coordinates into a body coordinate system, as opposed to a coordinate system with respect to the catheter itself.

In some embodiments, visualization, navigation, and mapping subsystem 18 includes a magnetic field-based system. For example visualization, navigation, and mapping subsystem 18 may include an electrical field- and magnetic field-based system such as the EnSite™ Precision™ system commercially available from Abbott Laboratories, and generally shown with reference to U.S. Pat. No. 7,263,397 entitled "Method and Apparatus for Catheter Navigation and Location and Mapping in the Heart", the entire disclosure of which is incorporated herein by reference. In such embodiments, distal end 28 may include at least one magnetic field sensor—e.g., magnetic coils (not shown). If two or more magnetic field sensors are disposed near ablation electrode 82, a full six-degree-of-freedom registration of magnetic and spatial coordinates could be accomplished without having to determine orthogonal coordinates by solving for a registration transformation from a variety of positions and orientations. Further benefits of such a configuration may include advanced dislodgement detection and deriving dynamic field scaling since they may be self-contained.

In yet another embodiment of distal end 28 illustrated in FIG. 5, distal ring electrode $30_C$ may be omitted and spot electrodes $30_B$ may be located in its place. As a result, spot electrodes $30_B$ would be closer to ablation electrode 82, which would provide positioning coordinates closer to ablation electrode 82. This in turn may provide for more accurate and precise calculation of the position of ablation electrode 82. Additionally, just as if the distal ring electrode $30_C$ were still in place, a mean signal from the spot electrodes $30_B$ and the proximal ring electrode $30_A$ could still be used to obtain bipolar EP data.

Figure 6:
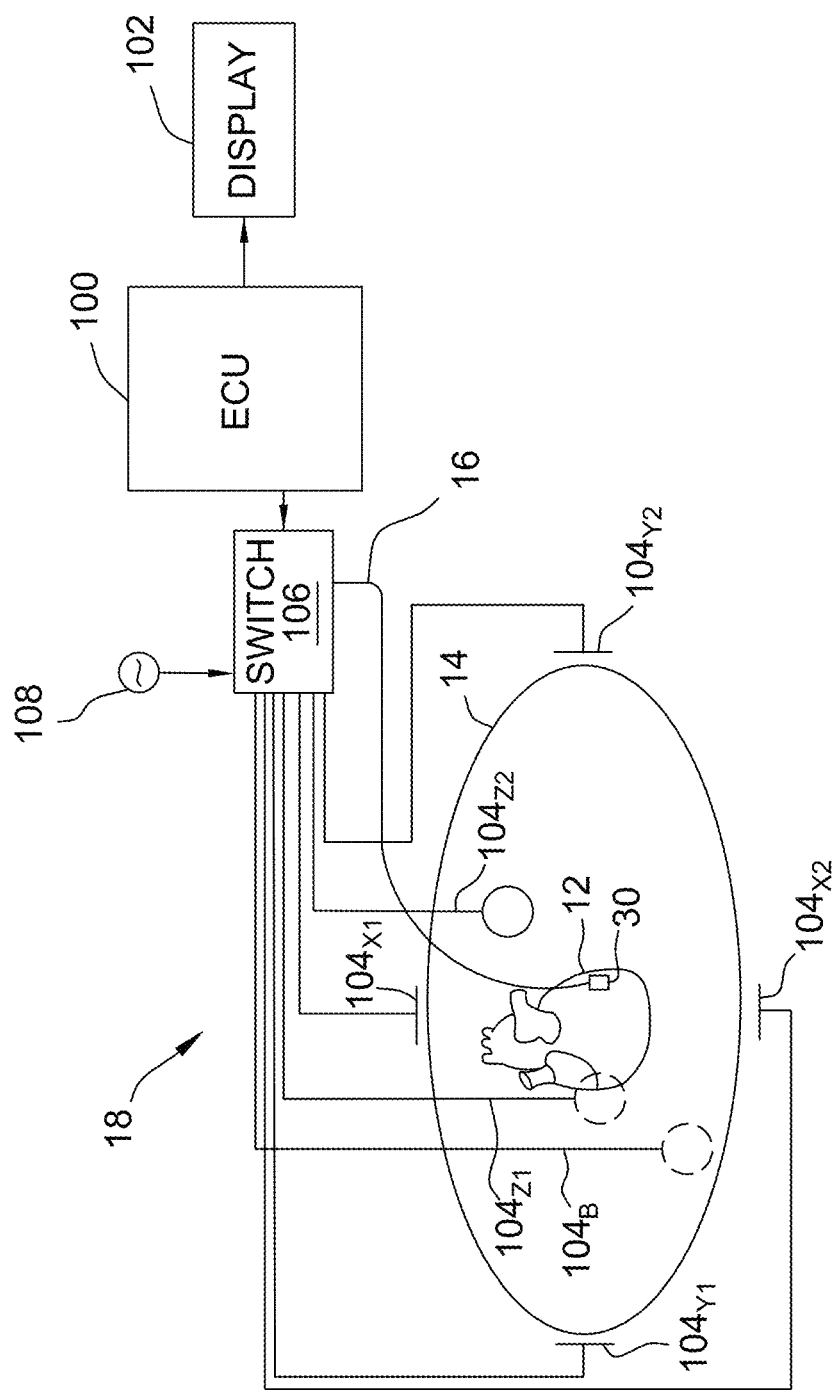
FIG. 6 is a schematic and diagrammatic view of one embodiment of a visualization, navigation, and mapping subsystem that may be used with the system shown in FIG. 1.

With reference to FIGS. 1 and 6, the visualization, navigation, and mapping subsystem 18 will now be described. The visualization, navigation, and mapping subsystem 18 is provided for visualization, navigation, and/or mapping of internal body structures and/or medical devices. In an exemplary embodiment, the subsystem 18 may contribute to the functionality of the system 10 in two principal ways. First, the subsystem 18 may provide the system 10 with a geometrical anatomical model representing at least a portion of the tissue 12. Second, the subsystem 18 may provide a means by which the position coordinates (x, y, z) of the electrodes 30 (or generally, sensors) may be determined as they measure EP data for analyses performed as part of the system 10. In certain embodiments, positioning sensors (e.g., electrical-field based or magnetic-field based) that are fixed relative to the electrodes 30 are used to determine the position coordinates. The positioning sensors provide the subsystem 18 with positioning data sufficient to determine the position coordinates of the electrodes 30. In other embodiments, position coordinates may be determined from the electrodes 30 themselves by using, for example, voltages measured by the electrodes 30.

Visualization, navigation, and mapping subsystem 18 may utilize an electric field-based system, such as, for example, the ENSITE NAVX™ system commercially available from Abbott Laboratories, and as generally shown with reference to U.S. Pat. No. 7,263,397 titled "Method and Apparatus for Catheter Navigation and Location and Mapping in the Heart," the entire disclosure of which is incorporated herein by reference, or the ENSITE VELOCITY™ system running a version of the NAVX™ software.

In other exemplary embodiments, subsystem 18 may utilize systems other than electric field-based systems. For example, subsystem 18 may comprise a magnetic field-based system such as the CARTO™ system commercially available from Biosense Webster, and as generally shown with reference to one or more of U.S. Pat. No. 6,498,944 entitled "Intrabody Measurement"; U.S. Pat. No. 6,788,967 entitled "Medical Diagnosis, Treatment and Imaging Systems"; and U.S. Pat. No. 6,690,963 entitled "System and Method for Determining the Location and Orientation of an Invasive Medical Instrument," the disclosures of which are incorporated herein by reference in their entireties.

In yet another exemplary embodiment, subsystem 18 may include a magnetic field-based system such as the GMPS system commercially available from MediGuide Ltd., and as generally shown with reference to one or more of U.S. Pat. No. 6,233,476 entitled "Medical Positioning System"; U.S. Pat. No. 7,197,354 entitled "System for Determining the Position and Orientation of a Catheter"; and U.S. Pat. No.

7,386,339 entitled "Medical Imaging and Navigation System," the disclosures of which are incorporated herein by reference in their entireties.

In a further exemplary embodiment, subsystem 18 may utilize a combination electric field-based and magnetic field-based system as generally shown with reference to U.S. Pat. No. 7,536,218 entitled "Hybrid Magnetic-Based and Impedance Based Position Sensing," the disclosure of which is incorporated herein by reference in its entirety. In yet still other exemplary embodiments, the subsystem 18 may comprise or be used in conjunction with other commonly available systems, such as, for example and without limitation, fluoroscopic, computed tomography (CT), and magnetic resonance imaging (MRI)-based systems.

In one embodiment wherein subsystem 18 includes an electric field-based system, and as described above, catheter 16 includes a plurality of electrodes 30 configured to both acquire EP data and produce signals indicative of catheter position and/or orientation information (positioning data). Subsystem 18 may use, for example and without limitation, time-division multiplexing or other similar techniques such that positioning data indicative of the position of electrodes 30 is measured intermittently with EP data. Thus, an electric field used to locate electrodes 30 may be activated between measurements of EP data, and electrodes 30 may be configured to measure both EP data and the electric field from subsystem 18, though at different times.

In other embodiments, however, wherein electrodes 30 may not be configured to produce positioning data, catheter 16 may include one or more positioning sensors in addition to electrodes 30. In one such embodiment, catheter 16 may include one or more positioning electrodes configured to generate signals indicative of the 3-D position or location of the positioning electrode(s). Using the position of the positioning electrode(s) along with a known configuration of catheter 16 (e.g., the known spacing between the positioning electrode(s) and electrodes 30) the position or location of each electrode 30 can be determined.

Alternatively, in another embodiment, rather than including an electric-field based system, subsystem 18 includes a magnetic field-based system. In such an embodiment, catheter 16 may include one or more magnetic sensors (e.g., coils) configured to detect one or more characteristics of a low-strength magnetic field. The detected characteristics may be used, for example, to determine a 3-D position or location for the magnetic sensors(s), which may then be used with a known configuration of the catheter 16 to determine a position or location for each electrode 30.

For purposes of clarity and illustration only, subsystem 18 will be described hereafter as comprising an electric field-based system, such as, for example, the ENSITE NAVX™ or VELOCITY™ systems identified above. Further, the description below will be limited to an embodiment of system 10 wherein electrodes 30 are configured to both acquire EP data and produce positioning data. It will be appreciated in view of the above, however, that the present disclosure is not meant to be limited to an embodiment wherein subsystem 18 includes an electric field-based system or electrodes 30 serve a dual purpose or function. Accordingly, embodiments wherein subsystem 18 is other than an electric field-based system, and catheter 16 includes positioning sensors in addition to electrodes 30 remain within the spirit and scope of the present disclosure.

With reference to FIGS. 1 and 6, in this embodiment subsystem 18 may include an electronic control unit (ECU) 100 and a display device 102. Alternatively, one or both of ECU 100 and display device 102 may be separate and distinct from, but electrically connected to and configured for communication with, subsystem 18. Subsystem 18 may still further include a plurality of patch electrodes 104, among other components. With the exception of a patch electrode $104_B$ called a "belly patch," patch electrodes 104 are provided to generate electrical signals used, for example, in determining the position and orientation of catheter 16, and in the guidance thereof. Catheter 16 may be coupled to ECU 100 or subsystem 18 with a wired or wireless connection.

In one embodiment, patch electrodes 104 are placed orthogonally on the surface of body 14 and are used to create axes-specific electric fields within body 14. For instance, patch electrodes $104_{X1}$, $104_{X2}$ may be placed along a first (x) axis. Patch electrodes $104_{Y1}$, $104_{Y2}$ may be placed along a second (y) axis, and patch electrodes $104_{Z1}$, $104_{Z2}$ may be placed along a third (z) axis. These patches may act as a pair or dipole. In addition or in the alternative, the patches may be paired off an axis or paired in series, e.g., $104_{X1}$ is paired with $104_{Y1}$, then $104_{Y2}$, $104_{Z1}$, $104_{Z2}$. In addition, multiple patches may be placed on one axis, e.g., under the patient. Each of the patch electrodes 104 may be coupled to a multiplex switch 106. In this embodiment, ECU 100 is configured, through appropriate software, to provide control signals to switch 106 to thereby sequentially couple pairs of electrodes 104 to a signal generator 108. Excitation of each pair of electrodes 104 generates an electric field within body 14 and within an area of interest such as tissue 12. Voltage levels at the non-excited electrodes 104, which are referenced to the belly patch $104_B$, are filtered and converted and provided to ECU 100 for use as reference values.

With electrodes 30 electrically coupled to ECU 100, electrodes 30 are placed within electrical fields that patch electrodes 104 create in body 14 (e.g., within the heart) when patch electrodes 104 are excited. Electrodes 30 experience voltages that are dependent on the respective locations between patch electrodes 104 and the respective positions of electrodes 30 relative to tissue 12. Voltage measurement comparisons made between electrodes 30 and patch electrodes 104 can be used to determine the position of each electrode 30 relative to tissue 12. Accordingly, ECU 100 is configured to determine position coordinates (x, y, z) of each electrode 30. Further, movement of electrodes 30 near or against tissue 12 (e.g., within a heart chamber) produces information regarding the geometry of tissue 12.

The information relating to the geometry of the tissue 12 may be used, for example, to generate models and/or maps of anatomical structures that may be displayed on a display device, such as, for example, display device 102. Information received from electrodes 30 can also be used to display on display device 102 the location and orientation of the electrodes 30 and/or the tip of catheter 16 relative to tissue 12. Accordingly, among other things, ECU 100 may provide a means for generating display signals for display device 102 and for creating a graphical user interface (GUI) on display device 102. It should be noted that in some instances where the present disclosure refers to objects as being displayed on the GUI or display device 102, this may actually mean that representations of these objects are being displayed on GUI or the display device 102.

It should also be noted that while in an exemplary embodiment ECU 100 is configured to perform some or all of the functionality described above and below, in another exemplary embodiment, ECU 100 may be separate and distinct from subsystem 18, and subsystem 18 may have another ECU configured to perform some or all of the functionality described herein. In such an embodiment, that ECU could be electrically coupled to, and configured for communication with, ECU 100. However, for purposes of clarity and illustration only, the description below will be limited to an embodiment wherein ECU 100 is shared between subsystem 18 and system 10 and is configured to perform the functionality described herein. Still further, despite reference to a "unit," ECU 100 may include a number or even a considerable number of components (e.g., multiple units, multiple computers, etc.) for achieving the exemplary functions described herein. In some embodiments, then, the present disclosure contemplates ECU 100 as encompassing components that are in different locations.

ECU 100 may include, for example, a programmable microprocessor or microcontroller, or may comprise an application specific integrated circuit (ASIC). ECU 100 may include a central processing unit (CPU) and an input/output (I/O) interface through which ECU 100 may receive a plurality of input signals including, for example, signals generated by patch electrodes 104 and positioning sensors. ECU 100 may also generate a plurality of output signals including, for example, those used to control display device 102 and switch 106. ECU 100 may be configured to perform various functions, such as those described in greater detail above and below, with appropriate programming instructions or code. Accordingly, in one embodiment, ECU 100 is programmed with one or more computer programs encoded on a computer-readable storage medium for performing the functionality described herein.

In addition to the above, ECU 100 may further provide a means for controlling various components of system 10 including, but not limited to, switch 106. In operation, ECU 100 generates signals to control switch 106 to thereby selectively energize patch electrodes 104. ECU 100 receives positioning data from catheter 16 reflecting changes in voltage levels and from the non-energized patch electrodes 104. ECU 100 uses the raw positioning data produced by patch electrodes 104 and electrodes 30, and corrects the data to account for respiration, cardiac activity, and other artifacts using known or hereinafter developed techniques. The corrected data, which comprises position coordinates corresponding to each of electrodes 30 (e.g., (x, y, z)), may then be used by ECU 100 in a number of ways, such as, for example and without limitation, to create a geometrical anatomical model of an anatomical structure or to create a representation of catheter 16 that may be superimposed on a map, model, or image of tissue 12 generated or acquired by ECU 100.

ECU 100 may be configured to construct a geometrical anatomical model of tissue 12 for display on display device 102. ECU 100 may also be configured to generate a GUI through which a user may, among other things, view a geometrical anatomical model. ECU 100 may use positioning data acquired from electrodes 30 or other sensors on distal end 28 or from another catheter to construct the geometrical anatomical model. In one embodiment, positioning data in the form of a collection of data points may be acquired from surfaces of tissue 12 by sweeping distal end 28 of catheter 16 along the surfaces of tissue 12. From this collection of data points, ECU 100 may construct the geometrical anatomical model. One way of constructing the geometrical anatomical model is described in U.S. patent application Ser. No. 12/347,216 entitled "Multiple Shell Construction to Emulate Chamber Contraction with a Mapping System," the entire disclosure of which is incorporated herein by reference. Moreover, the anatomical model may comprise a 3-D model or a two-dimensional (2-D) model. As will be described in greater detail below, a variety of information may be displayed on the display device 102, and in the GUI displayed thereon, in particular, in conjunction with the geometrical anatomical model, such as, for example, EP data, images of catheter 16 and/or electrodes 30, metric values based on EP data, HD surface maps, and HD composite surface maps.

To display the data and images that are produced by ECU 100, display device 102 may include one or more conventional computer monitors other display devices well known in the art. It is desirable for display device 102 to use hardware that avoids aliasing. To avoid aliasing, the rate at which display device 102 is refreshed should be at least as fast as the frequency with which ECU 100 is able to continuously compute various visual aids, such as, for example, HD surface maps.

As described above, the plurality of electrodes 30 disposed at distal end 28 of catheter 16 are configured to acquire EP data. The data collected by the respective electrodes 30 may be collected simultaneously. In one embodiment, EP data may include at least one electrogram. An electrogram indicates the voltage measured at a location (e.g., a point along tissue 12) over a period of time. By placing a high density of electrodes 30 on distal end 28, ECU 100 may acquire a set of electrograms measured from adjacent locations in tissue 12 during the same time period. The adjacent electrode 30 locations on distal end 28 may collectively be referred to as a "region."

ECU 100 may also acquire times at which electrograms are measured, the positions from which electrograms are measured, and the distances between electrodes 30. As for timing data, ECU 100 may track, maintain, or associate timing data with the voltages of each electrode 30 as measured. In addition, the 3-D position coordinates of each electrode 30 as it measures voltages may be determined, for example, as described above by visualization, navigation, and mapping subsystem 18. ECU 100 may be configured to continuously acquire position coordinates of electrodes 30, especially when electrodes 30 are measuring EP data. Because ECU 100 may know the spatial distribution of electrodes 30 of each distal end 28 configuration (e.g., matrix-like, spiral, basket, etc.), ECU 100 may recognize from the position coordinates of electrodes 30 which configuration of distal end 28 is deployed within a patient. Furthermore, the distances between electrodes 30 may be known by ECU 100 because electrodes 30 may be precisely and strategically arranged in a known spatial configuration. Thus, if distal end 28 is not deformed, a variety of analyses may use the known distances between electrodes 30 without having to obtain the coordinate positions from the subsystem 18 to solve for the distances between electrodes 30.

With ECU 100 having voltage, timing, and position data corresponding to respective electrodes 30 in addition to the known electrode 30 spatial configuration, many comparative temporal and spatial analyses may be performed, as described below. Some of these analyses lead to creation of HD surface maps representing activation patterns from tissue 12, which are possible in part because of the high density of electrodes 30 at distal end 28 of shaft 24. By providing a high density of electrodes at distal end 28, the accuracy and resolution of HD surface maps produced by system 10 are enhanced.

With respect to capturing or collecting EP data measured by the high density of electrodes 30, in one embodiment, ECU 100 may be programmed to continuously record and analyze data in real-time or near real-time. In another embodiment, a user may specify through a user input device a time window (e.g., 200 ms, 30 seconds, 10 minutes etc.)

during which ECU 100 may capture data measured from electrodes 30. The user input device may include, for example and without limitation, a mouse, a keyboard, a touch screen, and/or the like. It should be noted that in one embodiment, electrodes 30 may continuously measure voltages along tissue 12, and ECU 100 may selectively capture or record such voltages from electrodes 30. In still another embodiment, electrodes 30 measure voltages in accordance with a sampling rate or command from ECU 100. Once distal end 28 of shaft 24 is positioned near or along tissue 12 as desired, the user could prompt a trigger for the time window. The user may configure the trigger for the time window to correspond, for example, to a particular cardiac signal or the expiration of a timer. To illustrate, trigger could be set so ECU 100 records data from electrodes 30 before, during, and after an arrhythmia breakout or disappearance. One possible way to capture the data occurring just prior to the particular cardiac signal would be to use a data buffer that stores data (which may later be obtained) for an amount of time.

ECU 100 may be configured to recognize particular cardiac signals to trigger the time window. To that end, electrodes 30 may constantly measure EP data when positioned near tissue 12. This may be the case even if the user has not prompted the trigger for the time window. For example, ECU 100 may recognize that distal end 28 is near tissue 12 inside body 14 based on the continuous measurements in the range of voltages that are expected near tissue 12. Or ECU 100 may, for example, be configured to constantly monitor voltages from electrodes 30 when ECU 100 is powered "on." In any event, ECU 100 may continuously acquire EP data and continuously assess patterns and characteristics in the EP data. For example, metrics based on EP data include, for example, local activation time (LAT), depolarization amplitude voltage (e.g., peak-to-peak amplitude (PP)), complex fractionated electrogram (CFE) activity, dominant frequency (DF), Fast Fourier Transform (FFT) ratio, activation potential, diastolic potential, and late potential. U.S. Pat. No. 9,186,081 entitled "System and Method for Diagnosing Arrhythmias and Directing Catheter Therapies", the disclosure of which is incorporated herein by reference in its entirety, discloses multiple examples of metrics based on EP data.

In the embodiments described herein, ECU 100 determines a prevalence of a cardiac phenomenon at one or more locations on tissue 12, as described herein. For example, ECU 100 may determine an area with consistent activation, an area with consistent turns where a wave front turns, and/or an area with consistent fast activation. Specifically, ECU 100 not only determines that the cardiac phenomenon occurs, but also determines how often the cardiac phenomenon occurs.

In at least some known systems, cardiac phenomena are detectable. However, the prevalence of those cardiac phenomena (i.e., how often those cardiac phenomena occur) is not determined. For example, rotors are one particular example of a cardiac phenomenon observable using the systems and methods described herein. If data is collected twenty times for a particular location on tissue 12, at least some known systems indicate that a rotor is present, regardless of whether the rotor was detected one of those twenty times, or eighteen of those twenty times. However, the longer the rotor persists, the more likely ablating the rotor will eliminate atrial fibrillation (AF). Thus, to aid clinicians, it would be desirable to be able to detect not only the presence, but also the prevalence, of one or more cardiac phenomena.

Figure 7:
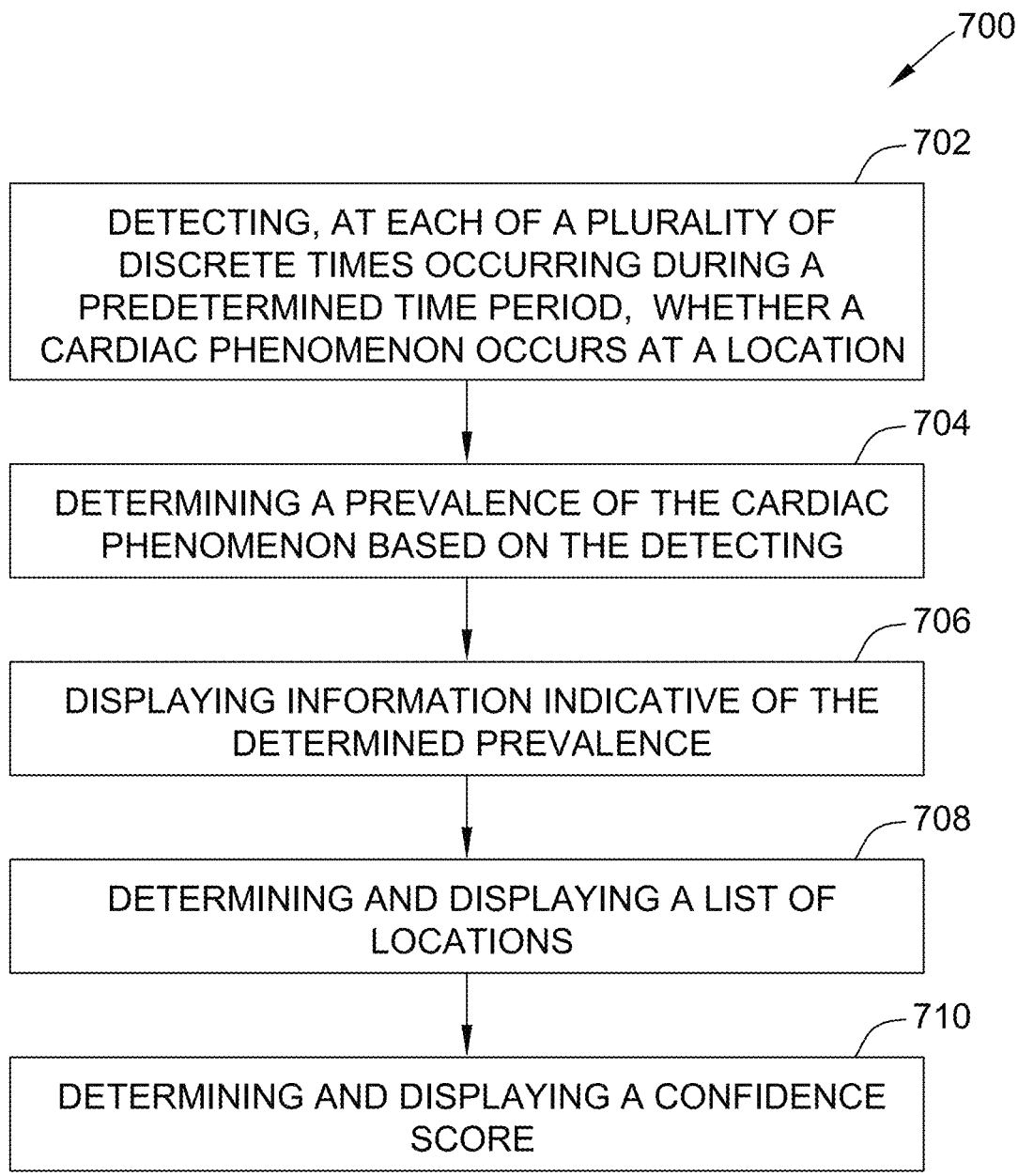
FIG. 7 is a flowchart of a method for determining prevalence of a cardiac phenomenon that may be used with the system shown in FIG. 6.

FIG. 7 is a flowchart of one embodiment of a method 700 for determining a prevalence of a cardiac phenomenon. As used herein, a 'cardiac phenomenon' may include any condition detectable or observable using system 10 (shown in FIG. 1). For example, in some embodiments, a cardiac phenomenon is a measured voltage that is within a predetermined range, above a predetermined threshold, or below a predetermined threshold. In other embodiments, a cardiac phenomenon is a rotor or driver (i.e., anatomical reentry generated by a wave propagating in a circular path). A rotor may be defined, for example, as an area where activation is relatively (e.g., more than 25%) circular. In other embodiments, the cardiac phenomenon is another detectable condition.

For example, certain metrics based on EP data are well known in the art, and may be the cardiac phenomenon detected using the embodiments described herein. These include, for example, local activation time (LAT), depolarization amplitude voltage (e.g., peak-to-peak amplitude (PP)), complex fractionated electrogram (CFE) activity, dominant frequency (DF), Fast Fourier Transform (FFT) ratio, activation potential, diastolic potential, late potential, etc. An LAT metric represents the difference in time between when a stationary reference electrode experiences a depolarization wavefront and when one or more roving electrodes (electrodes that are swept over or around tissue 12) experience the depolarization wavefront. A PP metric represents an amount of change between the highest peak voltage and the lowest trough voltage experienced by a specific point on tissue 12 during a depolarization wave. A CFE metric is described in U.S. Pat. No. 8,038,625 titled "System and Method for Three-Dimensional Mapping of Electrophysiology Information," the entire disclosure of which is incorporated herein by reference. A DF metric represents the most dominant frequency in a power spectrum analysis of a given interval of cardiac signal.

Method 700 may be conducted at a plurality of locations on tissue 12, or at a single location on tissue 12. Method 700 includes detecting 702, at each of a plurality of discrete times occurring during a predetermined time period, whether the cardiac phenomenon occurs at the location. As used herein, a location may refer to a discrete location, or to a region. A region may be defined, for example, by points within a predetermined distance of a central point, relative to anatomical structures (e.g., a region near a left vein, a region near a right vein, etc.), or using any suitable technique. In general, the more data acquired, the smaller the region sizes. In this embodiment, detection 702 is accomplished by processing, using ECU 100, data acquired by electrodes 30. Notably, any of the medical devices described above (e.g., the medical devices shown in FIGS. 2-5) may be used to acquire data for processing by ECU 100.

The predetermined time period may be any suitable time period over which the cardiac phenomenon is observable. For example, the predetermined time period may be as little as 30 seconds, as much as 10 minutes, or any other suitable duration. Of course, the longer the predetermined time period, the more stable the determination of the prevalence of the cardiac phenomenon. A sampling frequency (i.e., defining the intervals between the discrete times at which it is determined whether the cardiac phenomenon occurs) may also be any suitable sampling frequency. For example, the sampling frequency may be 1 Hertz (Hz) or 100 Hz. In some embodiments, the predetermined time period and/or the sampling frequency may be defined or selected by a user (e.g., using a user interface).

Method further includes determining 704 a prevalence of the cardiac phenomenon based on detecting 702. Specifically, in this embodiment, the prevalence is determined 704 as the number of discrete times when the cardiac phenomenon was detected, divided by the total number of discrete times. Accordingly, the prevalence may be expressed as a fraction or percentage. For example, if a rotor is observed at seven discrete times over a predetermined time period including a total of ten discrete times, the determined 704 prevalence would be 7/10, or 70%. In another example, if, over 100 cycles, a rotor is consistently in one area 17 of those cycles, the prevalence would be 17%.

Method further includes displaying 706 information indicative of the determined prevalence. The information may be displayed 706, for example, on display device 102 (shown in FIG. 6). In one embodiment, the displayed 706 information includes a color map projected onto a two-dimensional or three-dimensional geometric anatomical model. For example, locations having a high prevalence (e.g., greater than 75%) of the cardiac phenomenon may be displayed in a first color (e.g., black), locations having a moderate prevalence (e.g., between 25% and 75%) of the cardiac phenomenon may be displayed in a second color (e.g., gray), and locations have a low prevalence (e.g., less than 25%) of the cardiac phenomenon may be displayed in a third color (e.g., white). Alternatively, any suitable color scheme may be used. The ranges of what is considered high, moderate, and low prevalence will generally depend on the particular cardiac phenomena being observed. Further, in some embodiments, ECU 100 may automatically estimate what particular cardiac phenomena is being observed, and, based on this determination, adjust the prevalence ranges accordingly.

Figure 8:
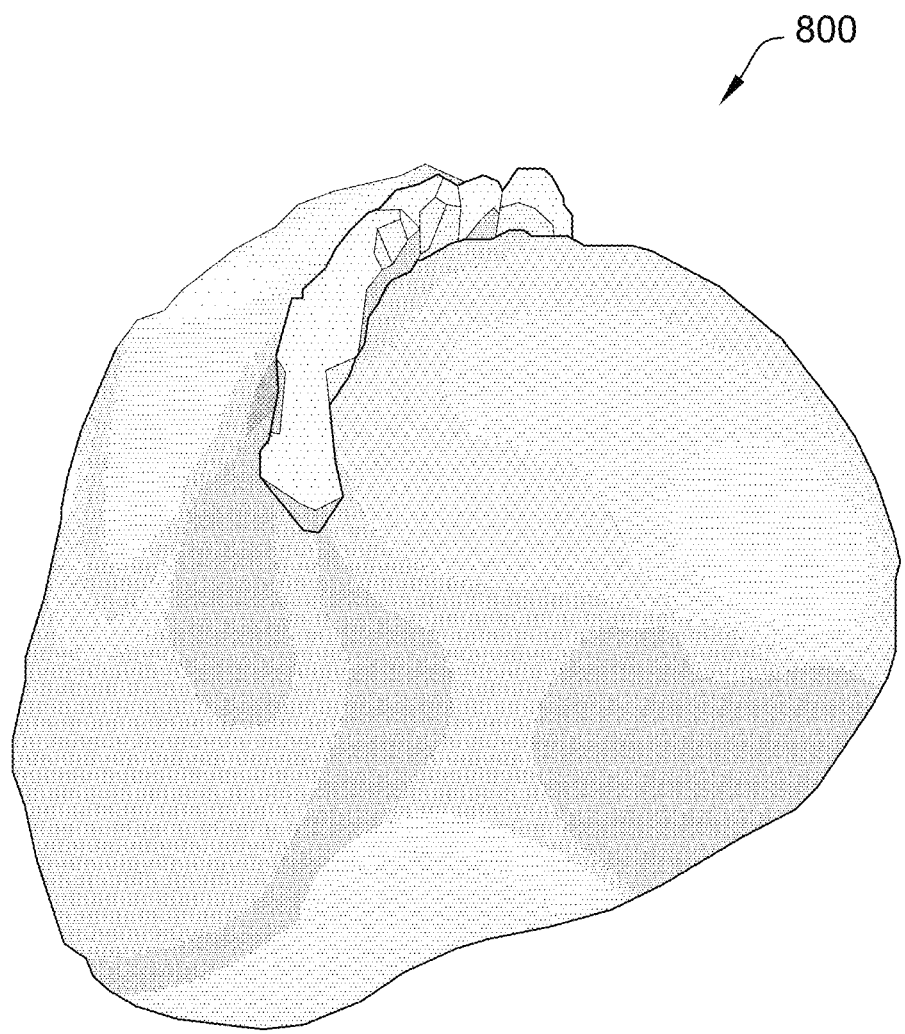
FIG. 8 is one embodiment of a graphical user interface showing a color map projected onto a three-dimensional anatomical model that may be generated using the system shown in FIG. 6.

From the displayed information, a clinician can quickly and easily determine which anatomical areas have a high prevalence of the cardiac phenomenon of interest. Further, the clinician can choose an ablation location based on the displayed 706 information. For example, ablating a first area where a rotor is detected with a high prevalence may be more effective in eliminating AF than ablating a second area where a rotor is detected with a low prevalence. FIG. 8 is one embodiment of a graphical user interface 800 showing a color map projected onto a three-dimensional anatomical model. As shown in FIG. 8, areas having different prevalence of the cardiac phenomenon are displayed differently (e.g., in a different color).

In some embodiments, ECU determines and displays 708 a list of locations (i.e., exact locations or regions) including the cardiac phenomenon. The list may be ranked, for example, in order of most prevalent to least prevalent. For example, if the cardiac phenomenon is a complex fractionated atrial electrogram (CFAE) with a 70 millisecond (ms) gradient, a first area having a CFAE with a 70 ms gradient 90% of the time would be ranked higher than a second area having a CFAE with a 70 ms gradient 17% of the time. Further, if the cardiac phenomenon is a rotor, a first area where a rotor is detected 7% of the time would be ranked lower than a second area where a rotor is detected 25% of the time. Accordingly, clinicians can quickly determine at which location(s) the cardiac phenomenon is most prevalent.

In some embodiments, the determined prevalence value itself (e.g., 77%) for a location (i.e., for an exact location or a regions) is displayed 706 as the information indicative of the determined prevalence. A confidence score associated with the prevalence value may also be determined and displayed 710. Generally, the longer the predetermined period of time and the higher the sampling frequency, the greater the confidence score. The confidence score may be calculated, for example, by ECU 100.

In yet another embodiment, the displayed 706 information includes a notification that the cardiac phenomenon has been observed. In this embodiment, the notification is generated when the determined 704 prevalence is greater than a predetermined threshold. For instance, in one example, system 10 may only generate and display a notification indicating that a rotor is present if the rotor prevalence is greater than 50%. Those of skill in the art will appreciate that any suitable threshold comparison may be implemented using the systems and methods described herein. Further, in some embodiments, ECU 100 may estimate the likelihood of the cardiac phenomenon using a statistical analysis (e.g., a Bayesian-type analysis) and/or a database storing previously observed cardiac phenomena and the conditions under which those cardiac phenomena occurred. In addition, in some embodiments, ECU 100 may determine the prevalence/likelihood of multiple cardiac phenomena simultaneously.

Accordingly, in the embodiments described herein, a prevalence of a cardiac phenomenon (e.g., voltage value, rotor, CFAE, etc.) is determined, and information indicative of the determined prevalence is displayed to a user. This improves the quality of information available to a clinician (e.g., information used to determine an ablation location).

It should be understood that system 10, and particularly ECU 100, as described above, may include conventional processing apparatus known in the art, capable of executing pre-programmed instructions stored in an associated memory, all performing in accordance with the functionality described herein. It is contemplated that the methods described herein, including without limitation the method steps of embodiments of the invention, will be programmed in some embodiments, with the resulting software being stored in an associated memory and where so described, may also constitute the means for performing such methods. Implementation of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A system for determining prevalence of a cardiac phenomenon based on electrophysiological (EP) data from a tissue of a body, the EP data measurable at a plurality of locations by at least one sensor disposed on at least one medical device that is positionable near the tissue of the body, the system comprising:
    an electronic control unit (ECU) communicatively coupled to a display device and configured to:
    for each of the plurality of locations:
        detect, at each of a plurality of discrete times occurring during a predetermined time period, whether a cardiac phenomenon occurs at the location based on the EP data, the plurality of discrete times occurring at a sampling frequency that defines a regular interval between consecutive discrete times of the plurality of discrete times;
        determine a prevalence of the cardiac phenomenon based on the detecting by dividing a number of the plurality of discrete times when the cardiac phenomenon occurs by a total number of the plurality of discrete times; and
        display information indicative of the determined prevalence of the cardiac phenomenon on the display device.

2. The system of claim 1, wherein the cardiac phenomenon is at least one of a voltage value within a predetermined range, a rotor, a driver, a local activation time, and complex fractionated electrogram activity.

3. The system of claim 1, wherein the sampling frequency is in a range from 1 Hertz (Hz) to 100 Hz.

4. The system of claim 1, wherein to display information indicative of the determined prevalence, the ECU is configured to display a color map projected onto a model of the tissue, the color map displaying locations having a high prevalence in a first color, locations having a moderate prevalence in a second color, and locations having a low prevalence in a third color.

5. The system of claim 1, wherein to display information indicative of the determined prevalence, the ECU is configured to display a list of locations where the cardiac phenomenon occurred.

6. The system of claim 5, wherein the listed locations are ranked by the determined prevalence associated with each listed location.

7. The system of claim 1, wherein to display information indicative of the determined prevalence, the ECU is configured to display a notification for a location when the determined prevalence at that location is greater than a threshold prevalence level.

8. The system of claim 1, wherein the ECU is further configured to:
    determine a confidence score associated with the determined prevalence, the confidence score determined based on a length of the predetermined time period and the sampling frequency; and
    display the confidence score on the display device.

9. A computer-implemented method of determining prevalence of a cardiac phenomenon based on electrophysiological (EP) data from a tissue of a body, the EP data measured at a plurality of locations by at least one sensor disposed on at least one medical device that is positionable near the tissue of the body, the method comprising:
    for each of the plurality of locations:
        detecting, at each of a plurality of discrete times occurring during a predetermined time period, whether a cardiac phenomenon occurs at the location based on the EP data, the plurality of discrete times occurring at a sampling frequency that defines a regular interval between consecutive discrete times of the plurality of discrete times;
        determining a prevalence of the cardiac phenomenon based on the detecting by dividing a number of the plurality of discrete times when the cardiac phenomenon occurs by a total number of the plurality of discrete times; and
        displaying information indicative of the determined prevalence of the cardiac phenomenon.

10. The method of claim 9, wherein the cardiac phenomenon is one of a voltage value within a predetermined range, a rotor, a driver, a local activation time, and complex fractionated electrogram activity.

11. The method of claim 9, wherein the sampling frequency is in a range from 1 Hertz (Hz) to 100 Hz.

12. The method of claim 9, wherein displaying information indicative of the determined prevalence comprises displaying a color map projected onto a model of the tissue.

13. The method of claim 9, wherein displaying information indicative of the determined prevalence comprises displaying a list of locations where the cardiac phenomenon occurred.

14. The method of claim 13, wherein the listed locations are ranked by the determined prevalence associated with each listed location.

15. The method of claim 9, wherein displaying information indicative of the determined prevalence comprises displaying a notification for a location when the determined prevalence at that location is greater than a threshold prevalence level.

16. A processing apparatus for determining prevalence of a cardiac phenomenon based on electrophysiological (EP) data from a tissue of a body, the EP data measurable at a plurality of locations by at least one sensor disposed on at least one medical device that is positionable near the tissue of the body, the processing apparatus configured to:
    for each of the plurality of locations:
        detect, at each of a plurality of discrete times occurring during a predetermined time period, whether a cardiac phenomenon occurs at the location based on the EP data, the plurality of discrete times occurring at a sampling frequency that defines a regular interval between consecutive discrete times of the plurality of discrete times;
        determine a prevalence of the cardiac phenomenon based on the detecting by dividing a number of the plurality of discrete times when the cardiac phenomenon occurs by a total number of the plurality of discrete times; and
        cause information indicative of the determined prevalence of the cardiac phenomenon to be displayed on a display device.

17. The processing apparatus of claim 16, wherein the cardiac phenomenon is one of a voltage value within a predetermined range, a rotor, a driver, a local activation time, and complex fractionated electrogram activity.

18. The processing apparatus of claim 16, wherein the sampling frequency is in a range from 1 Hertz (Hz) to 100 Hz.

19. The processing apparatus of claim 16, wherein to cause information indicative of the determined prevalence to be displayed, the processing apparatus is configured to cause a color map projected onto a model of the tissue to be displayed.

20. The processing apparatus of claim 16, wherein to cause information indicative of the determined prevalence to be displayed, the processing apparatus is configured to cause a list of locations where the cardiac phenomenon occurred to be displayed.

* * * * *